(12) United States Patent
Devin-Baudoin et al.

(10) Patent No.: US 8,163,273 B2
(45) Date of Patent: *Apr. 24, 2012

(54) PROCESS FOR PERMANENTLY RESHAPING THE HAIR USING AMINOSILICONES

(75) Inventors: Priscille Devin-Baudoin, Vanves (FR); Anne Sabbagh, Rueil Malmaison (FR)

(73) Assignee: L'Oreal S.A., Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 10/116,144

(22) Filed: Apr. 5, 2002

(65) Prior Publication Data

US 2002/0187117 A1  Dec. 12, 2002

(30) Foreign Application Priority Data

Apr. 6, 2001  (FR) ...................................... 01 04727

(51) Int. Cl.
*A61Q 5/04* (2006.01)
(52) U.S. Cl. ................. 424/70.122; 424/70.1; 424/70.2; 424/70.12
(58) Field of Classification Search .................. 424/401, 424/70.1, 70.2, 70.6, 70.11, 70.12, 70.112; 514/63, 880

See application file for complete search history.

(56) References Cited

U.S. PATENT DOCUMENTS

| | | | |
|---|---|---|---|
| 4,185,087 | A | 1/1980 | Morlino |
| 4,770,873 | A * | 9/1988 | Wolfram et al. ............. 424/70.2 |
| 5,106,612 | A | 4/1992 | Maignan et al. |
| 5,154,918 | A | 10/1992 | Maignan et al. |
| 5,160,449 | A | 11/1992 | Halloran |
| 5,302,659 | A * | 4/1994 | Bindl et al. .................. 524/838 |
| 5,466,878 | A | 11/1995 | Junino et al. |
| 5,583,257 | A | 12/1996 | Junino et al. |
| 5,925,341 | A | 7/1999 | Cervantes et al. |
| 5,985,294 | A | 11/1999 | Peffly |
| 6,159,914 | A * | 12/2000 | DeCoster et al. ............. 510/119 |
| 6,177,090 | B1 | 1/2001 | Dubief et al. |

FOREIGN PATENT DOCUMENTS

| | | |
|---|---|---|
| EP | 0 354 835 | 2/1990 |
| EP | 0 455 185 | 11/1991 |
| EP | 0 530 974 | 3/1993 |
| GB | 2 141 454 | 12/1984 |
| JP | 58-39612 | 3/1983 |
| JP | 1-110611 | 4/1989 |
| JP | 5-112436 | 5/1993 |
| JP | 7-157416 | 6/1995 |
| JP | 9-151120 | 6/1997 |
| JP | 11-246365 | 9/1999 |

OTHER PUBLICATIONS

Handbook of Cosmetic Science and Technology, 1$^{st}$ Edition, Elsevier Advanced Technology, 1994, pp. 115 and 117.*
Poucher's Perfumes, Cosmetics and Soaps, 2000, Kluwer Academic Publishers, (10th ed. By Hilda Butler), p. 282.*
Patent Abstracts of Japan, vol. 1997, No. 10, Oct. 31, 1997 (JP 09 151120).
Patent Abstracts of Japan, vol. 014, No. 571, Dec. 19, 1990 (JP 02 250814).
English language Derwent Abstract of EP 0 368 763, May 16, 1990.
Priscille Devin-Baudoin & Anne Sabbagh, U.S. Appl. No. 10/290,189, filed Nov. 8, 2002.
Priscille Devin-Baudoin & Anne Sabbagh, U.S. Appl. No. 10/290,148, filed Nov. 8, 2002.
English language Derwent Abstract and a Full Machine English language Translation of JP 11 246365.
English language Derwent Abstract and a certified English language translation of JP 58 039612.
English language Derwent Abstract and a Full Machine English language Translation of JP 07 157416.
English language Derwent Abstract and a Full Machine English language Tranlsation of JP 05 112436.
English language Derwent Abstract and a Certified English language translation of JP 01 110611.
English language esp@cenet Abstract and a Full Machine English language Translation of JP 9-151120.

* cited by examiner

*Primary Examiner* — Gina C Yu
(74) *Attorney, Agent, or Firm* — Finnegan, Henderson, Farabow, Garrett & Dunner, L.L.P.

(57) ABSTRACT

An improvement of a process for permanently reshaping keratin fibres, comprising the application to the keratin fibres, before the reducing operation and/or after the fixing operation, of a pre-treatment and/or post-treatment cosmetic composition comprising, in a cosmetically acceptable vehicle, at least one aminosilicone microemulsion, the number-average primary size of the particles in the at least one microemulsion ranging from 3 to 70 nm.

13 Claims, No Drawings

PROCESS FOR PERMANENTLY RESHAPING THE HAIR USING AMINOSILICONES

The present invention relates to an improvement of a process for permanently reshaping keratin fibres, such as the hair, the said process being able to be used especially in professional hairstyling salons or privately, via the marketing of kits. The improvement of said process comprises novel pre-treatment and/or post-treatment cosmetic compositions.

For the purposes of the present invention, the expression "permanent reshaping process" is well-known by those skilled in the art to mean any long-lasting process for shaping, curling, straightening or relaxing the hair. For example, a "long-lasting" effect could range from about 2 to about 2.5 months, wherein such time period varies among individuals having differing hair quality, elasticity, etc. On the other hand, a long-lasting effect could also be as short as one to two weeks.

The expression "keratin fibres" in particular means the hair, the eyelashes and the eyebrows, with the most common example being the hair.

It is known that the most common technique for obtaining a permanent reshaping of the hair comprises, in a first stage, in opening the keratin —S—S— disulphide (cystine) bonds using a reducing composition containing a reducing agent (reduction step), followed, usually after having rinsed the hair thus treated, by reconstituting, in a second stage, the said disulphide bonds by applying to the hair, which has been placed under tension beforehand (curlers and the like), an oxidizing composition (oxidizing step, also known as the fixing step) so as to finally give the hair the desired shape. This technique thus makes it equally possible either to make the hair wavy or to straighten or relax it. The new shape given to the hair by a chemical treatment such as above can be remarkably long-lasting and can withstand the action of washing with water or shampoos, as opposed to simple standard techniques for temporary reshaping, such as hairsetting.

The reducing compositions that may be used to carry out the first step of a permanent-waving operation generally contain, as reducing agents, sulphites, bisulphites or thiols. Among the thiols that may be mentioned are cysteine and its various derivatives, cysteamine and its derivatives, thiolactic acid, thioglycolic acid and also its esters, especially glyceryl monothioglycolate, and thioglycerol.

As regards the oxidizing compositions required to carry out the fixing step, use is usually made in practice of compositions based on aqueous hydrogen peroxide solution or of alkali metal bromates.

A problem with the permanent-waving techniques known to date is that applying them repeatedly to the hair may induce in the long term a gradual deterioration in the quality of the hair, and especially a gradual and pronounced deterioration in the sheen and the cosmetic properties of the hair, such as the softness of the fibres, which have a tendency to become more and more coarse, and also as regards their disentangling, the hair becoming more and more difficult to disentangle. This deterioration can be pronounced when the fixing step of the permanent-waving operation is carried out using a bromate.

To limit this deterioration of the hair, it has already been proposed to introduce conditioners directly into the reducing composition. For example, Japanese patent applications H2-250814 and H9-151120 describe reducing compositions containing aminosilicones, which may optionally be in the form of a microemulsion.

However, processes for permanently reshaping the hair using such compositions are not entirely satisfactory, since the degree, the quality and liveliness of the curls can be insufficient and short-lived, as if the conditioner, especially aminosilicones, directly combined with the reducing agent, blocked the activity of the reducing agent.

The present invention seeks to provide a process for permanently reshaping keratin fibres, such as the hair, which reduces the degree of at least one of mechanical and cosmetic degradation of the hair, while at the same time providing at least one of satisfactory degree, satisfactory quality and satisfactory liveliness of curls.

The inventors have discovered, surprisingly and unexpectedly, that by applying to the hair, before applying the reducing composition and/or after having applied the oxidizing composition, at least one pre-treatment and/or post-treatment cosmetic composition comprising at least one aminosilicone microemulsion, one could solve at least one of the problems posed by the present invention.

One subject of the invention is a process for permanently reshaping keratin fibres, such as the hair, comprising:
(i) applying a reducing composition to the keratin fibres;
(ii) oxidizing the keratin fibres, and further comprising
applying to the keratin fibres, before applying operation (i) and/or after oxidizing operation (ii), a pre-treatment and/or post-treatment cosmetic composition comprising, in a cosmetically acceptable vehicle, at least one aminosilicone microemulsion, the number-average primary size of the particles in the at least one microemulsion ranging from 3 to 70 nm.

Another subject of the invention relates to a kit for permanently reshaping keratin fibres, one of the compartments comprising a pre-treatment and/or post-treatment cosmetic composition comprising at least one amino-silicone microemulsion, the number-average primary size of the particles in the at least one microemulsion ranging from 3 to 70 nm.

Furthermore, the inventors have also discovered, surprisingly and unexpectedly, that the application of at least one pre-treatment and/or post-treatment cosmetic composition containing said at least one aminosilicone microemulsion can impart at least one beneficial quality over time, for example, even after the permanently reshaped hair has been shampooed.

AMINOSILICONE MICROEMULSION

For the purposes of the present invention, the expression "aminosilicone microemulsion" means thermodynamically stable dispersions comprising a discontinuous phase formed by aminosilicones in a continuous phase formed by water, optionally combined with surfactants. As defined herein, the term microemulsion encompasses particles having a number-average primary size ranging from 3 to 70 nm.

The expression "primary size" means the maximum size that it is possible to measure between two diametrically opposite points on the particles.

For example, the number-average primary size of the particles in the microemulsion ranges from 5 to 60 nm and as a further example, ranges from 10 to 50 nm. As will be recognized by one skilled in the art, the number average primary size of the particles may be measured by a technique suitable for the size measurement being taken, for example, for particles essentially spherical, by scattering techniques such as static light scattering in which a laser granulometer such as MALVERN or an optical particle counter such as Coulter counter by Coultronix may be employed, and dynamic light scattering, in which a laser granulometer such as Brookhaven is employed.

In the text hereinbelow and hereinabove, in accordance with what is generally accepted, the terms "silicone" and "polysiloxane" are understood to be chosen from organosilicon polymers and oligomers having linear, cyclic, branched, and crosslinked structures of variable molecular weight, obtained by polymerization and/or polycondensation of suitably functionalized silanes, and comprising a repetition of main units in which the silicon atoms are linked together by oxygen atoms (siloxane bonding Si-O-Si), wherein substituted hydrocarbon-based radicals can be linked directly via a carbon atom to the said silicon atoms, to form, for example, an organomodified silicone. Representative hydrocarbon-based radicals can be chosen from alkyl radicals, especially C1-C10 alkyl radicals, such as methyl, fluoroalkyl radicals, aryl radicals such as phenyl, and alkenyl radicals such as vinyl; representative other types of radicals that can be linked, either directly or via a hydrocarbon-based radical, to the siloxane chain can be chosen from hydrogen, halogens such as chlorine, bromine and fluorine, thiols, alkoxy radicals, polyoxyalkylene (or polyether) radicals such as polyoxyethylene and polyoxypropylene, hydroxyl and hydroxyalkyl radicals, amide groups, acyloxy and acyloxyalkyl radicals, amphoteric and betain groups, and anionic groups such as carboxylates, thioglycolates, sulphosuccinates, thiosulphates, phosphates and sulphates.

According to the invention, the term "aminosilicone" denotes any silicone comprising at least one group chosen from primary, secondary, and tertiary amines and a quaternary ammonium group. Mention may thus be made of:

(a) polysiloxanes chosen from the formula:

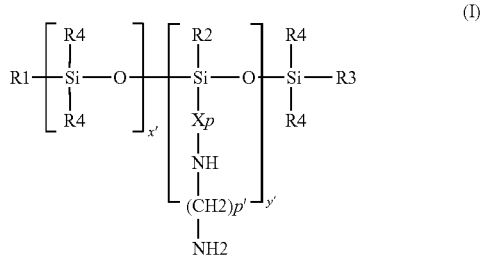

(I)

in which x' and y' are integers depending on the molecular weight, generally such that the weight-average molecular weight of these polysiloxanes of formula (I) ranges from about 5000 to about 500000;

R1, R2 and R3, which may be identical or different, are chosen from a hydroxyl radical, C1 to C4 alkyl radicals, C1 to C4 alkoxy radicals, and a phenyl radical;

X is chosen from branched and unbranched $C_1$-$C_4$ alkylene radicals;

R4, which may be identical or different, is chosen from $C_1$-$C_4$ alkyl radicals and a phenyl radical;

p and p', independently of each other, are chosen from integers ranging from 1 to 10.

For example, alkyl denotes methyl and alkoxy denotes methoxy.

For example, p=3, p'=2 and R4 denotes methyl and X denotes methylene.

Among these polymers, mention may be made of the compounds denoted by the name "amodimethicone" and "trimethylsilylaminodimethicone" in the CTFA dictionary.

(b) aminosilicones corresponding to the formula:

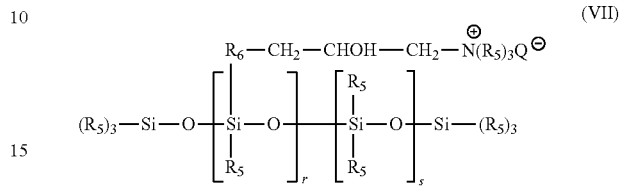

(VII)

in which $R_5$, which may be identical or different, is chosen from monovalent hydrocarbon-based radicals containing from 1 to 18 carbon atoms, such as $C_1$-$C_{18}$ alkyl radicals and $C_2$-$C_{18}$ alkenyl radicals, for example methyl;

$R_6$ is chosen from divalent hydrocarbon radicals, such as $C_1$-$C_{18}$ alkylene radicals and $C_1$-$C_{18}$ divalent alkylenoxy radicals, further such as $C_1$-$C_8$ radicals, linked to the Si via an SiC bond;

Q- is an anion, such as a halide ion, such as chloride, and further such as an organic acid salt (such as acetate);

r represents a mean statistical value from 2 to 20, such as from 2 to 8;

s represents a mean statistical value from 20 to 200 such as from 20 to 50.

Such aminosilicones are described more particularly in U.S. Pat. No. 4,185,087.

One silicone falling within this category is the silicone sold by the company Union Carbide under the name "Ucar Silicone ALE 56".

c) quaternary ammonium silicones of formula:

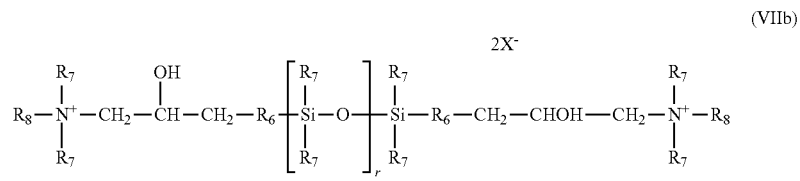

(VIIb)

in which $R_7$, which may be identical or different, is chosen from monovalent hydrocarbon-based radicals containing from 1 to 18 carbon atoms, such as $C_1$-$C_{18}$ alkyl radicals, for example methyl, $C_2$-$C_{18}$ alkenyl radicals, and rings comprising 5 to 6 carbon atoms;

$R_6$, which may be identical or different, is chosen from divalent hydrocarbon-based radicals, such as $C_1$-$C_{18}$ alkylene radicals, $C_1$-$C_{18}$ divalent alkylenoxy radicals, for example $C_1$-$C_8$ radicals, linked to the Si via an SiC bond;

$R_8$, which may be identical or different, is chosen from a hydrogen atom, monovalent hydrocarbon-based radicals containing from 1 to 18 carbon atoms, such as $C_1$-$C_{18}$ alkyl radicals, $C_2$-$C_{18}$ alkenyl radicals, and —$R_6$—NHCOR$_7$ radicals, wherein $R_6$ and $R_7$ are as defined above;

X— is an anion such as a halide ion, such as chloride, or an organic acid salt (such as acetate);

r represents a mean statistical value from 2 to 200 such as from 5 to 100.

These silicones are described, for example, in patent application EP-A-0 530 974.

According to the invention, the aminosilicone is, for example, one:
whose amine number is greater than 0.15 meq per gram, that has hydroxyl and/or alkoxy end groups.

An example of a microemulsion containing such a silicone that may be mentioned is the product sold by the company Wacker under the name Wacker Finish CT96E.

For example, the concentration of aminosilicone in the pre-treatment or post-treatment composition ranges from 0.05% to 10% by weight relative to the total weight of this composition, such as from 0.1% to 7%.

The microemulsions in accordance with the present invention may contain solvents.

These solvents can be, for example, chosen from:
$C_1$-$C_8$ lower alcohols such as ethanol;
glycols such as glycerol, propylene glycol, 1,3-butylene glycol, dipropylene glycol and polyethylene glycols containing from 4 to 16, such as from 8 to 12, ethylene oxide units.

The solvents can be, for example, present in the microemulsions of the invention in concentrations ranging from 0.01% to 30% by weight relative to the total weight of the emulsion.

In addition, the use of the alcohols as defined above, at concentrations of greater than or equal to 5% by weight such as greater than 15%, makes it possible to obtain microemulsions free of preserving agent.

The pre-treatment or post-treatment compositions comprising the microemulsions used according to the invention may contain active agents chosen from water-soluble and liposoluble active agents, having activity chosen from cosmetic and dermopharmaceutical activities. The liposoluble active agents are in the oily globules of the emulsion, whereas the water-soluble active agents are in the aqueous phase of the emulsion. Examples of active agents that may be mentioned include vitamins and derivatives thereof, such as vitamin E, vitamin E acetate, vitamin C and its esters, the B vitamins, vitamin A alcohol and retinol, vitamin A acid and retinoic acid and its derivatives, provitamins, such as panthenol, vitamin A palmitate, niacinamide, ergocalciferol, antioxidants, essential oils, wetting agents, silicone and non-silicone sunscreens, preserving agents, sequestering agents, pearlescent agents, pigments, moisturizers, antidandruff agents, anti-seborrhoeic agents, plasticizers, hydroxy acids, electrolytes and fragrances.

For example, the pH of the pre-treatment or post-treatment composition comprising an aminosilicone microemulsion can range from 2 to 10 such as from 3 to 9.

The pre-treatment composition comprising an aminosilicone microemulsion is applied to the hair to be treated, which will optionally have been moistened beforehand. This application may be performed after the usual step of placing the hair under tension in a shape corresponding to the desired final shape for the said hair (for example curls), this step itself possibly being carried out by any way, such as a mechanical way, that is suitable and known per se for maintaining hair under tension, such as, for example, rollers, curlers and the like.

For example, the pre-treatment or post-treatment composition comprising an aminosilicone microemulsion is left to act on the hair, at room temperature or under heat, for a period ranging from 1 to 60 minutes and further for example from 3 to 30 minutes.

According to an optional step of the process, the hair impregnated with the pre-treatment composition comprising an aminosilicone microemulsion can be rinsed, the rinsing generally being carried out using water.

In a step of the process according to the invention, a reducing composition is applied to the hair, the said reducing composition generally comprising at least one thiol.

The thiol in the reducing composition may be chosen from thiols known as reducing agents such as, for example, thioglycolic acid, glyceryl and glycol monothioglycolate, cysteamine and its $C_1$-$C_4$ acyl derivatives, such as N-acetylcysteamine and N-propionylcysteamine, cysteine, N-acetylcysteine, sugar N-mercaptoalkylamides, such as N-(2-mercaptoethyl) gluconamide, 3-mercaptopropionic acid and its derivatives, thiolactic acid and its esters, such as glyceryl monothiolactate, thiomalic acid, pantethine, thioglycerol, alkali metal and alkaline-earth metal sulphites and biosulphites, the N-(mercaptoalkyl)—hydroxyalkylamides described in patent application EP-A-354835 and the N-mono- and N,N-dialkylmercapto-4-butyramides described in patent application EP-A-368763, the aminomercaptoalkylamides described in patent application EP-A-432 000, the N-(mercaptoalkyl)succinamic acid and N-(mercaptoalkyl)succinimide derivatives described in patent application EP-A-465342, the alkylaminomercaptoalkylamides described in patent application EP-A-514282, and the mixture of 2-hydroxypropyl thioglycolate and of 2-hydroxy-1-methylethyl thioglycolate described in patent application FR-A-2679448.

Thioglycolic acid, thiolactic acid and 3-mercaptopropionic acid are representative reducing agents.

The reducing agents can, for example, be present in a concentration ranging from 1% to 20% by weight relative to the total weight of the reducing composition.

The pH of the reducing composition can, for example, range from 6 to 10 such as from 7 to 9.

The pH values of the reducing compositions may be conventionally adjusted by adding basifying agents such as, for example, aqueous ammonia, monoethanolamine, diethanolamine, triethanolamine, isopropanolamine, 1,3-propanediamine, ammonium and alkali metal carbonates and bicarbonates, primary, secondary and tertiary amine carbonates and bicarbonate and organic carbonates, such as guanidine carbonate. Needless to say all these compounds can be use alone or in a mixture.

The reducing composition may be in a form chosen from thickened and unthickened lotions, creams, gels, and any other suitable form and may contain additives known for their use in reducing compositions for permanently reshaping the hair.

The reducing composition may also be of the exothermic type, that is to say of the type causing a certain level of heating during application to the hair, affording a pleasant sensation to the person on whom the permanent-waving or straightening operation is being performed.

The reducing composition may also contain a solvent such as, for example, ethanol, propanol, isopropanol, and glycerol, for example, in a concentration no greater than 20% relative to the total weight of the composition.

When the compositions are intended for a hair straightening or relaxing operation, the reducing composition can, for example, be in the form of a thickened cream so as to keep the hair as straight as possible. These creams are prepared in the form of "heavy" emulsions, for example based on glyceryl stearate, glycol stearate, self-emulsifying waxes, fatty alcohols, etc.

It is also possible to use liquids or gels containing thickeners such as carboxyvinyl copolymers which "stick" the hairs together and keep them in the smooth position during the exposure time.

The compositions may also be in a "self-neutralizing" or "self-regulated" form and, in this case, the reducing agents used according to the invention are combined with at least disulphide known for its use in a reducing composition for self-neutralizing permanent waving.

In a conventional manner, the hair onto which the reducing composition has been applied should be left to rest for a few minutes, such as from 2 to 40 minutes and further such as from 5 to 30 minutes, so as to allow the reducing agent sufficient time to act correctly on the hair. This waiting stage is generally carried out by leaving the treated hair to rest in the open air (at room temperature or with heating). During this waiting stage, care is generally taken to ensure that the hair does not dry out completely but instead remains humid.

The hair impregnated with the reducing composition can then be carefully rinsed, generally with water. Optionally, after rinsing, a stage of heating at high temperature for a few seconds is carried out.

Next, an oxidizing composition is applied to the hair thus rinsed, with the aim of fixing the new shape given to the hair. It may also be envisaged to leave the hair to be oxidized by the air.

The oxidizing composition comprises an oxidizing agent that may be chosen from aqueous hydrogen peroxide solution, alkali metal bromates, persalts, and polythionates. As mentioned previously, one of the great advantages of the process according to the invention is that it is entirely suitable in the case of bromate-based oxidizing compositions. The bromate concentration in the oxidizing composition can range, for example, from 0.1 to 2 M.

The pH of the oxidizing composition can range, for example, from 2 to 10.

As in the case of the application of the reducing composition, the hair onto which the oxidizing composition has been applied is then, conventionally, left for a standing or waiting stage that may last a few minutes, for example, from 3 to 30 minutes and as a further example, from 5 to 15 minutes.

The post-treatment composition comprising an aminosilicone microemulsion can, for example, be applied, after rinsing out the oxidizing composition, to wet or dry hair. The hair that has undergone the post-treatment may optionally be dried and/or heated and/or rinsed, before being styled. Where appropriate, the composition may be applied while the hair is maintained by a mechanical device, such as hairsetting rollers and curlers.

Usually, the hair impregnated with the oxidizing composition is rinsed carefully, generally with water. Before or after rinsing, the keratin fibres are separated from whatever device was used for placing them under tension.

The head of hair finally obtained has good cosmetic properties. The hair can be one of shinier, softer, easier to disentangle, and easier to style.

For example, the pre-treatment or post-treatment composition comprising an aminosilicone microemulsion is applied according to at least one of the following variants:
  to clean, wet hair, before using a device for placing the hair under tension, without rinsing the hair before applying the reducing agent;
  to wet hair after rinsing out the fixing agent, the hair being subsequently either rinsed or dried.

When the process for permanently reshaping the hair is a straightening process, it is possible, in a manner that is known per se, to use a straightening agent, such as thiol agents and alkaline agents.

In the case of a thiol straightening agent, the process in accordance with the invention can, for example, be carried out by applying the pre-treatment or post-treatment composition containing an aminosilicone microemulsion according to at least one of the following variants:
  to clean, wet hair, without rinsing before applying the reducing agent;
  to clean, wet hair, after rinsing out the fixing agent, by rinsing before drying the hair.

In the case of an alkaline straightening agent, the process in accordance with the invention can be, for example, carried out by applying the pre-treatment or post-treatment composition comprising an aminosilicone microemulsion to wet hair, after rinsing out neutralizing shampoo, by rinsing before drying the hair.

In the case of a hair curling operation, the process in accordance with the invention can give lively curls and the hair can be one of supple, light, silky, and well separated.

In the case of a hair straightening operation, the process in accordance with the invention can provide at least one of the following: afford control of the body of the hair, make the hair smooth from the root to the end, and give a more natural feel.

The invention may be understood more clearly with the aid of the non-limiting examples which follow, which constitute illustrative embodiments of the process according to the invention.

a.m. means active material.

EXAMPLES

Example 1

Use is made of a pre-treatment composition containing the aminosilicone microemulsion at 2% final weight of a.m. Wacker Finish CT96E (Wacker), the number-average primary size of the particles being 20 nm. This composition is applied to a lock of moderately sensitized, clean wet hair. The lock is passed under heat, at 60° C. for 15 minutes, and then rinsed. It then undergoes a treatment with the permanent-waving product Dulcia Vital 2® for sensitized hair, sold by L'Oréal. The same permanent-waving treatment is applied in parallel to a lock not treated with the pre-treatment composition. The alkaline solubility and porosity measurements are collated in Table 1.

TABLE 1

|  | Alkaline solubility | Porosity |
| --- | --- | --- |
| Process according to the invention | 22% | 55 |
| Comparative Process | 26% | 59 |

It is found that the pre-treatment in accordance with the present invention has the effect of reducing the degradation of the hair, after the action of the permanent-waving product.

To measure the alkaline solubility (AS), the process is performed as follows: the hair to be analysed is treated with a solution of 10N sodium hydroxide, heated at 65° C. for 30 minutes. The alkaline solubility is the percentage by mass of hair lost during this treatment.

To measure the porosity, the process is performed as follows: the hair to be analysed is placed in a solution containing an uncharged dye (2-nitro-para-phenylenediamine), drained and then desorbed in two buffered aqueous solutions. The absorbence A of these combined desorbing solutions is measured at 470 nm. The porosity is obtained by the relationship: 100×A−20.

Example 2

A pre-treatment lotion containing 2% Wacker Finish CT96E silicone active material is used. The lotion is applied to wet hair, held in shape by curlers, and a bonnet is put on. The hair is passed under a heating hood for 5 minutes. The bonnet is removed and the hair is rinsed. The permanent-waving treatment is then applied in a conventional manner, using Dulcia Vital 2.

This process is applied to six individuals, having natural hair, in a half-head test in comparison with a permanent-waving product Dulcia Vital 2, and makes it possible to obtain an improvement in the softness, the liveliness of the curls, the bouffant appearance of the hair and the feel. As the hair undergoes shampoo washes in the course of time, the cosmetic differences resulting from the present invention are maintained for about six weeks.

Example 3

A pre-treatment lotion containing 2% of Wacker Finish CT96E silicone active material is used. The hair is left for 15 minutes under heat. A Stiff thiolactic acid hair-straightening cream is then applied. The rest of the straightening operation is carried out in a conventional manner.

This process, applied to five individuals as a half-head test in comparison with the Stiff hair-straightening agent, gives an improvement in the softness, disentangling and ease of styling, and better control of the hair's body. After several shampoo washes, the hair treated with the composition in accordance with the present invention is softer and less bouffant.

Example 4

A pre-treatment lotion containing 2% of Wacker Finish CT96E silicone active material is used, on wet hair that has previously undergone a straightening treatment with Goldys without sodium hydroxide. The hair thus treated is left for 10 minutes at room temperature, and the composition is then rinsed out. This process, applied to 11 individuals with frizzy natural hair, in a half-head test in comparison with the straightening agent Goldys without sodium hydroxide, gives an improvement in the softness and disentangling and good control of the hair's body, after each shampoo wash, and the side treated with the aminosilicone composition in accordance with the present invention is softer and easier to disentangle.

Example 5

A pre-treatment lotion containing 2% of Wacker Finish CT96E silicone active material is used, after rinsing out the fixing agent. The hair is placed in shape by means of blow-drying, without rinsing out this composition. This process, applied to five individuals with very sensitized hair, in a half-head test in comparison with a standard permanent-waving product, gives an improvement in the disentangling, softness, liveliness, curliness, feel and body on the day of the application. In the six weeks following this permanent-waving operation, the curliness disappears more quickly on the side not treated with the silicone in accordance with the present invention. The half-head treated with the silicone microemulsion always remains markedly softer and easier to disentangle, the hair is easier to style and is more bouffant.

What is claimed is:

1. A process for permanently reshaping keratin fibres comprising:
   (i) optionally applying a pre-treatment cosmetic composition to said keratin fibres;
   (ii) applying a reducing composition to the keratin fibres;
   (iii) oxidizing the keratin fibres;
   (iv) optionally applying a post-treatment cosmetic composition to said keratin fibres;
   wherein at least one of steps (i) and (iv) is performed and wherein said pre-treatment and/or post-treatment cosmetic compositions comprise, in a cosmetically acceptable vehicle, at least one aminosilicone microemulsion, wherein the number-average primary size of the particles in said at least one microemulsion ranges from 3 to 70 nm, and wherein the aminosilicone is chosen from compounds of formula I:

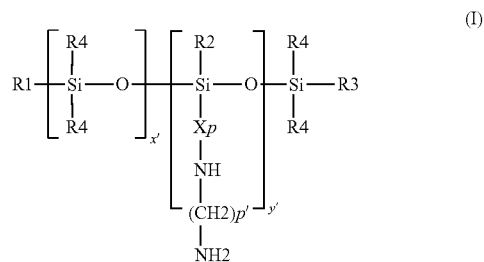

in which x' and y' are integers such that the weight-average molecular weight of said aminosilicone ranges from about 5000 to about 500000;

$R_1$, $R_2$ and $R_3$, which may be identical or different, are chosen from a hydroxyl radical, $C_1$ to $C_4$ alkyl radicals, $C_1$ to $C_4$ alkoxy radicals, and a phenyl radical;

X is chosen from branched and unbranched $C_1$-$C_4$ alkylene radicals;

$R_4$, which may be identical or different, is chosen from $C_1$-$C_4$ alkyl and phenyl radicals; and p and p', independently of each other, are chosen from integers ranging from 1 to 10, provided that at least one of $R_1$, $R_2$ and $R_3$ is chosen from hydroxyl radicals and $C_1$ to $C_4$ alkoxy radicals; and wherein said aminosilicone comprises an amine number greater than 0.15 meq per gram.

2. The process according to claim 1, wherein said keratin fibres are hair.

3. The process according to claim 1, wherein the number-average primary size of the particles in said at least one microemulsion ranges from 5 to 60 nm.

4. The process according to claim 3, wherein the number-average primary size of the particles in said at least one microemulsion ranges from 10 to 50 nm.

5. The process according to claim 1, wherein the pH of the pre-treatment and/or post-treatment composition comprising the at least one aminosilicone microemulsion ranges from 2 to 10.

6. The process according to claim 5, wherein the pH of the pre-treatment and/or post-treatment composition comprising the at least one aminosilicone microemulsion ranges from 3 to 5.

7. The process according to claim 1, wherein the aminosilicone concentration in the pre-treatment and/or post-treatment compositions ranges from 0.05% to 10% by weight, wherein said aminosilicone concentration is relative to the total weight of this composition.

8. The process according to claim 7, wherein the aminosilicone concentration in the pre-treatment and/or post-treatment compositions ranges from 0.1% to 7% by weight, wherein said aminosilicone concentration is relative to the total weight of this composition.

9. The process according to claim 2, wherein the pre-treatment and/or post-treatment compositions comprising the at least one aminosilicone microemulsion is left to act on the hair for a time period ranging from 1 to 60 minutes.

10. The process according to claim 9, wherein the pre-treatment and/or post-treatment compositions comprising the at least one aminosilicone microemulsion is left to act on the hair for a time period ranging from 3 to 30 minutes.

11. The process according to claim 1, wherein the pre-treatment and/or post-treatment compositions further comprise additives chosen from vitamins, vitamin derivatives, provitamins, antioxidants, essential oils, wetting agents, silicone and non-silicone sunscreens, preserving agents, sequestering agents, pearlescent agents, pigments, moisturizers, antidandruff agents, anti-seborrhoeic agents, plasticizers, hydroxy acids, electrolytes, and fragrances.

12. The process according to claim 11, wherein said vitamins and vitamin derivatives are chosen from vitamin E, vitamin E acetate, vitamin C and its esters, the B vitamins, vitamin A alcohol and retinol, vitamin A acid. and retinoic acid and its derivatives.

13. The process according to claim 11, wherein the provitamins are chosen from panthenol, vitamin A palmitate, niacinamide, and ergocalciferol.

\* \* \* \* \*